United States Patent [19]

Annen et al.

[11] Patent Number: 4,912,098
[45] Date of Patent: Mar. 27, 1990

[54] ANTIINFLAMMATORY 6 ALPHA-METHYLHYDROCORTISONES

[75] Inventors: Klaus Annen; Karl Petzoldt; Henry Laurent; Rudolf Wiechert; Helmut Hofmeister, all of Berlin, Fed. Rep. of Germany

[73] Assignee: Schering Aktiengesellschaft, Berlin and Bergkamen, Fed. Rep. of Germany

[21] Appl. No.: 92,825

[22] Filed: Sep. 3, 1987

Related U.S. Application Data

[63] Continuation of Ser. No. 854,239, Apr. 21, 1986, abandoned, which is a continuation of Ser. No. 549,376, Nov. 7, 1983, abandoned, which is a continuation of Ser. No. 499,713, Dec. 14, 1982, abandoned, which is a continuation of Ser. No. 334,026, Dec. 23, 1981, abandoned.

[30] Foreign Application Priority Data

Dec. 23, 1980 [DE]  Fed. Rep. of Germany ....... 3049400

[51] Int. Cl.⁴ .......................... A61K 31/56; C07J 9/00
[52] U.S. Cl. ................................. 514/179; 260/397.45
[58] Field of Search .................... 514/179; 260/397.45

[56] References Cited

U.S. PATENT DOCUMENTS 4,264,585  4/1981  Baumgarth et al. ................ 424/243
4,290,962  9/1981  Tachi et al. ..................... 260/397.45

OTHER PUBLICATIONS

Spero et al., Journal Amer. Chem. Soc., 78 (1956), pp. 6213-6214.

Primary Examiner—Leonard Schenkman
Attorney, Agent, or Firm—Millen, White & Zelano

[57] ABSTRACT $6\alpha$-methylhydrocortisones of Formula I

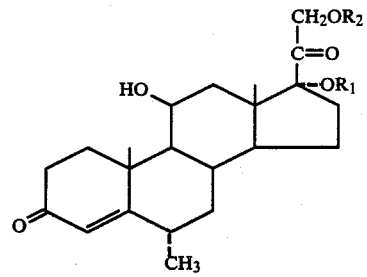

wherein
  $R_1$ is alkanoyl of 2-6 carbon atoms or benzoyl and
  $R_2$ is hydrogen or alkanoyl of 2-6 carbon atoms
have valuable antiinflammatory properties.

5 Claims, No Drawings

ANTIINFLAMMATORY 6 ALPHA-METHYLHYDROCORTISONES

This is a continuation of Ser. No. 854,239 filed Apr. 21, 1986, now abandoned which is a continuation of Ser. No. 549,376 filed Nov. 7, 1983, now abandoned which is a continuation of Ser. No. 449,713 filed Dec. 14, 1982, now abandoned which is a continuation of original application Ser. No. 334,026 filed Dec. 23, 1981, now abandoned.

BACKGROUND OF THE INVENTION

The present invention relates to 6α-methylhydrocortisones, their preparation and use.

6α-methylhydrocortisone and its 21-esters are known [J. Amer. Chem. Soc. 78: 6213 f (1956)]. They are of considerable importance as intermediates for the synthesis of 6α-methylprednisolone. Not much attention was given to 6α-methylhydrocortisone as a pharmacologically active agent per se. It is systematically more effective than hydrocortisone, but less effective than 6α-methylprednisolone [J. Amer. Chem. Soc. 78: 6214 (1956)].

SUMMARY OF THE INVENTION

It is an object of this invention to provide new 6α-methylhydrocortisones having valuable pharmacological properties.

These objects have been achieved by providing 6α-methylhydrocortisones of formula I

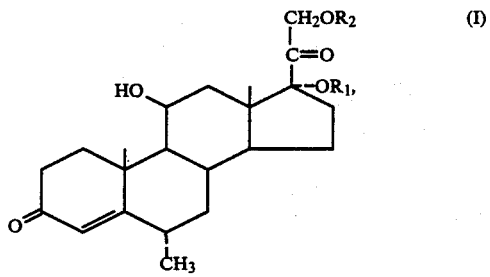

wherein
$R_1$ is 1-oxoalkyl of 2-6 carbon atoms or benzoyl and $R_2$ is hydrogen or 1-oxoalkyl of 2-6 carbon atoms.

Upon further study of the specification and appended claims, further objects and advantages of this invention will become apparent to those skilled in the art.

DETAILED DISCUSSION

The novel 6α-methylhydrocortisone derivatives of Formula I can carry, as the 1-oxoalkyl (alkanoyl) groups of 2-6 carbon atoms for either $R_1$ and/or $R_2$, for example, acetyl, propionyl, butyryl, isobutyryl, valeryl, 3-methylbutyryl, trimethylacetyl, and the like. $R_1$ can also be benzoyl.

It has now been found that the 6α-methylhydrocortisone derivatives of this invention upon topical administration, surprisingly, possess a significantly stronger antiinflammatory efficacy than the corresponding derivatives of hydrocortisone per se. This efficacy is frequently significantly stronger than that of difluorinated "thoroughbred corticoids" such as, for example, 6α,9α-difluoro-11β-hydroxy-16α-methyl-21-valeryloxy-1,4-pregnadiene-3,20-dione (="Nerisona"). However, upon systemic administration, these 6α-methylhydrocortisone derivatives, surprisingly, are not of any significantly stronger efficacy than the corresponding derivatives of hydrocortisone per se.

The novel 6α-methylhydrocortisone derivatives of this invention, consequently, are suitable, for administration to mammals, including humans, in combination with the excipients customary in galenic pharmacy, for the local treatment of contact dermatitis, eczemas of a great variety of types, neurodermatoses, erythrodermia, burns, pruritus valvae et ani, rosacea, erythematodes cutaneus, psoriasis, lichen ruber planus et verrucosus, and similar skin diseases.

The special drug preparations are produced in the usual way by mixing the active agents with suitable additives to produce the desired form for administration, e.g.: solutions, lotions, ointments, creams, or plasters. In the thus-formulated medicines, the concentration of active ingredient is dependent on the form of administration. For lotions and ointments, an active agent concentration of 0.001% to 1% is preferably employed.

Moreover, the novel compounds are also highly suitable for the preparation of inhalants, optionally in combination with the usual vehicles and auxiliary agents; these inhalants can be used for therapy in allergic diseases of the respiratory tract, e.g., bronchial asthma or rhinitis.

The novel corticoids are also orally administrable in the form of capsules, tablets, or dragees, containing preferably 10-200 mg of active ingredient; or, rectally administrable in the form of suspensions containing preferably 100-500 mg of active ingredient per dosage unit; they are, thus, also suitable for the treatment of allergic diseases of the intestinal tract, such as colitis ulcerosa or colitis granulomatosa.

In general, the administration of the compound of this invention is fully conventional and analogous, e.g., to the corresponding administration of the conventional steroidal corticoids for the same purpose, e.g., such as hydrocortison-17-butyrate.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for any use can be determined using conventional considerations, e.g., by customary comparison of the differential activities of the subject compound and of a known agent, e.g., by means an appropriate, conventional pharmacological protocal.

The novel 6α-methylhydrocortisone derivatives of this invention can be prepared by conventional methods. For example, compounds of formula Ia

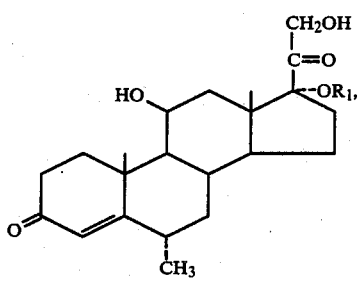

wherein
$R_1$ is 1-oxoalkyl of 2–6 carbon atoms, can be conventionally prepared by (a) fermenting a 6α-methyl steroid of Formulae II or III

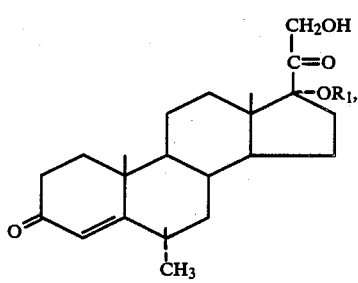

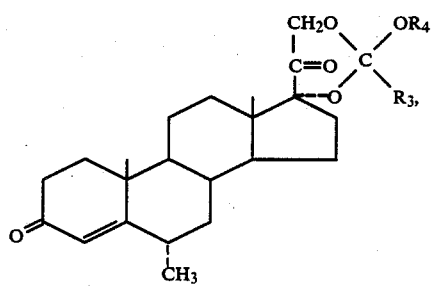

wherein
$R_1$ is as defined above,
$R_3$ is alkyl of 1–5 carbon atoms or phenyl, and
$R_4$ is alkyl of 1–4 carbon atoms, with a fungal culture of the genus Curvularia at a pH of 4.0–7.0; or
(b) hydrolyzing a 6α-methylhydrocortisone orthocarboxylic acid ester of Formula IV

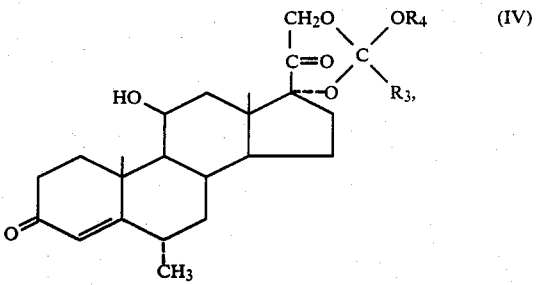

wherein $R_3$ and $R_4$ are as defined above or
(c) rearranging a 6α-methylhydrocortisone 21-acylate of Formula V

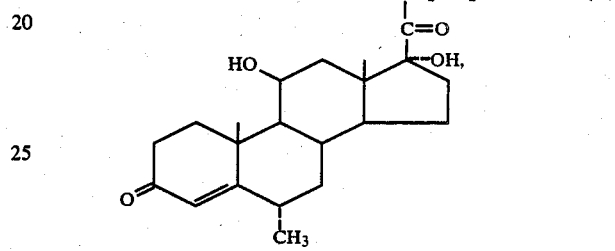

wherein $R'_2$ is 1-oxoalkyl of 2–6 carbon atoms into the corresponding 17-acylate.

Moreover, 6α-methylhydrocortisones of Formula Ib

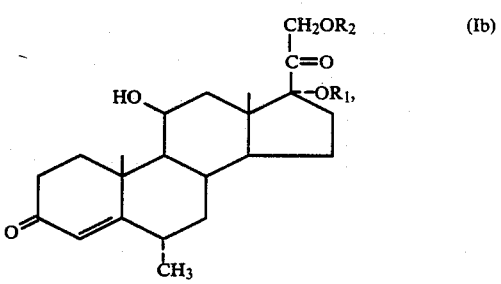

wherein
$R_1$ is oxoalkyl of 2–6 carbon atoms or benzoyl and
$R'_2$ is 1-oxoalkyl of 2–6 carbon atoms can be prepared conventionally by
(a) esterifying a 6α-methylhydrocortisone 17-acylate of Formula Ia

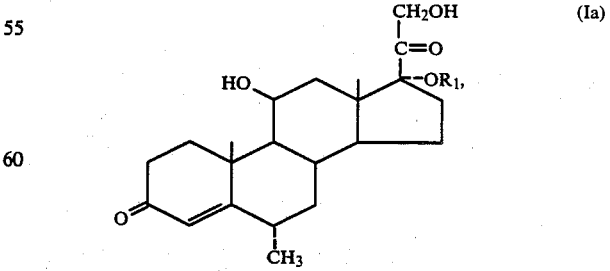

wherein $R_1$ is as defined above, in the 21-position with an alkanecarboxylic acid of 2–6 carbon atoms or with a reactive derivative thereof; or (b) etherifying a 6α-methylhydrocortisone 21-acylate of Formula V

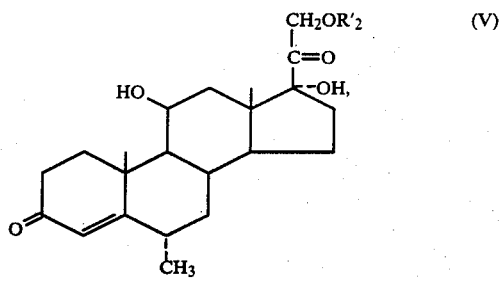

wherein R'$_2$ is as defined above, in the 11-position with a trialkylsilyl compound or esterifying it with a derivative of a strongly acidic monocarboxylic acid. Thereafter, the 17-position is acylated with a carboxylic acid chloride or a carboxylic acid anhydride in the presence of 4-dimethylaminopyridine; and the blocking group in the 11-position is split off.

These methods can be conducted under fully conventional conditions such as those described in German published Patent Applications No. 16 18 599; 26 45 104; 26 45 105; 23 40 591 and 19 58 549, as well as in U.S. Pat. No. 3,383,394, the British Patents 1131146 and 1440063 and the South African Patents 7705915 and 7705914. The disclosures of all of these are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 100 g of 17,21-dihydroxy-6α-methyl-4-pregnene-3,20-dione and 10 g of pyridinium tosylate are dissolved in 700 ml of dimethylformamide at room temperature and under agitation, and the clear solution is diluted with 3.5 l of toluene. The solution is then warmed up in a glycerin bath and, at a temperature of 120° C., 1.2 l of toluene is distilled off to remove traces of water. Under agitation, 240 ml of trimethyl orthoformate is gradually poured into the hot reaction solution; the latter is reacted for 30 minutes and thereafter additional toluene and other readily volatile reaction components are removed by 1 hour of distillation. The mixture is combined with 120 ml of pyridine, cooled to 60° C., and concentrated under vacuum at a bath temperature of 70° C. The mixture is then diluted with 400 ml of dimethylformamide, and the solution is poured under agitation into 10 l of water, thus obtaining the product in the form of a yellowish-white, crystalline precipitate. The mixture is stirred for another 2 hours, vacuum-filtered, washed with water, and dried for 24 hours at 40° C. in a vacuum drying cabinet over phosphorus pentoxide, thus obtaining 111.6 g of 17,21-(1-methoxyethylidenedioxy)-6α-methyl-4-pregnene-3,20-dione, mp 85°–87° C.

(b) A 7–14 day old sweetwort slant with Curvularia lunata (NRRL 2380) is freed of the supernatant with 3 ml of physiological sodium chloride solution, and this supernatant is used to inoculate a 2-liter Erlenmeyer flask containing 500 ml of a nutrient solution of 2% glucose and 2% cornsteep, sterilized for 30 minutes at 120° C. in an autoclave and adjusted to pH 6.5. After 60 hours of shaking on a rotary shaker at 30° C., 250 ml of this germination culture is used to inoculate the preliminary fermentor. A 20-liter prefermentor charged with 15 l of a nutrient medium of the same composition as the germination medium and sterilized at 121° C. and 1 bar gauge pressure is inoculated with 250 ml of germination culture. With the addition of silicone SH as the defrother, germination is now conducted up to 29° C. and 0.6 bar pressure under aeration (15 l/min) and agitation (220 rpm) for 24 hours. The main fermentor is inoculated with 1.5 l of this prefermentor culture. A 20-liter main fermentor, filled with 13.5 l of a sterilized nutrient medium made up of 3% cornsteep liquor and 0.7% glucose, adjusted to pH 5.5, is inoculated with 1.5 l of prefermentor culture. After an incubation phase of 12 hours under prefermentation conditions, a sterile-filtered solution of 12.18 g of 17,21-(1-methoxyethylidenedioxy)-6α-methyl-4-pregnene-3,20-dione in 130 ml of dimethylformamide is added thereto and the mixture is further agitated and aerated. Four hours after addition of the substrate, the pH value of the culture broth is set at pH 4.5 and held at this value ± pH 0.2 by automatic control with 16% sodium hydroxide solution and 20% sulfuric acid until the end of the fermentation. After a contact period of 51 hours, the microbiological conversion is complete. The content of the fermentor is then treated in a continuous centrifuge, and the culture filtrate as well as the centrifuged fungal mycelium are extracted separately with methyl isobutyl ketone. The extracts are combined and first concentrated in a forced-circulation evaporator to 1 liter at 40° C. under vacuum, and then entirely evaporated to dryness in a 2-liter round flask on a rotary evaporator under vacuum at a bath temperature of 40° C. The remaining oily residue is combined with 400 ml of hexane and decanted after vigorous shaking. Subsequently, the residue is once again combined with 400 ml of hexane and agitated at room temperature for 2 hours. The now completely crystallized residue is vacuum-filtered, washed with 100 ml of hexane, and dried for 4 hours at 60° C. in a vacuum drying cabinet. Yield: 9.9 g of 17-acetoxy-11β,21-dihydroxy-6α-methyl-4-pregnene-3,20-dione which, after recrystallization from acetonediisopropyl ether, melts at 192°–194° C.

EXAMPLE 2

(a) 15.0 g of 11β,71,21-trihydroxy-6α-methyl-4-pregnene-3,20-dione and 1.5 g of pyridinium tosylate are dissolved under heating in 120 ml of dimethylformamide and 1,050 ml of benzene (toluene). At a bath temperature of 140° C., 450 ml of benzene (toluene) is distilled off via a water trap; the solution is briefly cooled to 80° C. and combined with 36 ml of ethyl orthopropionate. Within 20 minutes, the residual benzene (toluene) is distilled off together with the readily volatile solvent components. After adding 18 ml of pyridine, the mixture is concentrated under vacuum, thus obtaining 17,21-(1-ethoxypropylidenedioxy)-11β-hydroxy-6α-hydroxy-6α-methyl-4-pregnene-3,20-dione as an oil.

(b) A suspension of the above crude product in 450 ml of methanol is refluxed with a mixture of 18 ml of 0.1-molar aqueous sodium acetate solution and 162 ml of 0.1N aqueous acetate acid for 1 hour at 100° C. The mixture is concentrated to turbidity, poured on water, and extracted with a large amount of ethyl acetate. The organic phase is washed with water, dried over sodium sulfate, and evaporated to dryness under vacuum. The crude product is purified on 650 g of silica gel with a methylene chloride-acetone gradient (0–20% acetone), thus obtaining 11.2 g of 11β,21-dihydroxy-6α-methyl-17-propionyloxy-4-pregnene-3,20-dione, mp 197° C.

EXAMPLE 3

(a) Analogously to Example 2(a), 15.0 g of 11β,17,21-trihydroxy-6α-methyl-4-pregnene-3,20-dione is reacted with trimethyl orthobutyrate to obtain 11β-hydroxy-17,21-(1-methoxybutylidenedioxy)-6α-methyl-4-pregnene-3,20-dione.

(b) The crude 11β-hydroxy-17,21-(1-methoxybutylidenedioxy)-6α-methyl-4-pregnene-3,20-dione is treated analogously to Example 2(b) with a buffer solution, worked up, and purified. Yield: 11.4 g of 17-butyryloxy-11β,21-dihydroxy-6α-methyl-4-pregnene-3,20-dione, mp 176° C.

EXAMPLE 4

At 0° C. under argon, 40 ml of a 5% solution of methyllithium in ether is added dropwise to a suspension of 9.3 g of copper(I) iodide in 186 ml of anhydrous tetrahydrofuran. The yellow solution is cooled to −30° C., and a solution of 7.4 g of 11β,17-dihydroxy-6α-methyl-21-valeryloxy-4-pregnene-3,20-dione in 186 ml of anhydrous tetrahydrofuran is added thereto. The mixture is agitated for 10 minutes at −25° C. and poured on an aqueous ammonium chloride solution. After extraction with methylene chloride, the organic solution is washed, dried over sodium sulfate, and evaporated under vacuum. The crude product is purified on 600 g of silica gel with a methylene chloride-acetone gradient (0–20% acetone), thus isolating 4.6 g of 11β,21-dihydroxy-6α-methyl-17-valeryloxy-4-pregnene-3,20-dione, mp 160° C.

EXAMPLE 5

7.7 g of 11β,17-dihydroxy-21-isobutyryloxy-6α-methyl-4-pregnene-3,20-dione is rearranged analogously Example 4 with lithium dimethyl cuprate, worked up, and purified, thus obtaining 5.8 g of 11β,21-dihydroxy-17-isobutyryloxy-6α-methyl-4-pregnene-3,20-dione, mp 191° C.

EXAMPLE 6

Under the conditions of Example 4, 7.3 g of 11β,17-dihydroxy-6α-methyl-21-trimethylacetoxy-4-pregnene-3,20-dione is rearranged, worked up, and purified, resulting in 1.7 g of 11β,21-dihydroxy-6α-methyl-17-trimethylacetoxy-4-pregnene-3,20-dione.

EXAMPLE 7

(a) 7.0 g of 11β,17,21-trihydroxy-6α-methyl-4pregnene-3,20-dione is reacted analogously to Example 2(a) with triethyl orthobenzoate to obtain 17,21-(1-ethoxybenzylidenedioxy)-11β-hydroxy-6α-methyl-4-pregnene-3,20-dione.

(b) The crude 17,21-(1-ethoxybenzylidenedioxy)-11β-hydroxy-6α-methyl-4-pregnene-3,20-dione is hydrolyzed, worked up, and purified under the conditions of Example 2(b). Yield: 4.6 g of 17-benzoyloxy-11β,21-dihydroxy-6α-methyl-4pregnene-3,20-dione, mp 214° C.

EXAMPLE 8

A solution of 1.0 g of 17-acetoxy-11β,21-dihydroxy-6α-methyl-4-pregnene-3,20-dione in 20 ml of pyridine is combined with 3 ml of butyric anhydride and stirred at room temperature for 2 hours. The reaction solution is then allowed to flow into 150 ml of cooled 8% sulfuric acid and agitated for another 5 hours; the product, initially precipitated in oily form, becomes completely crystallized. The product is vacuum-filtered, washed with water, and dried for 6 hours at 80° C. in a vacuum drying cabinet. For purifying purposes, the crude product is recrystallized from acetone-diisopropyl ether, thus obtaining 940 mg of 17-acetoxy-21-butyryloxy-11β-hydroxy-6α-methyl-4-pregnene-3,20-dione, mp 98°–120° C.

EXAMPLE 9

A solution of 1.0 g of 11β,21-dihydroxy-6α-methyl-17-propionyloxy-4-pregnene-3,20-dione in 10 ml of pyridine is agitated with 5 ml of propionic anhydride for 2 hours at room temperature. The mixture is then poured on an ice water-sodium chloride solution, the precipitate is filtered off and, after the usual working-up process, the crude product is purified on 65 g of silica gel with a methylene chloride-acetone gradient (0–15% acetone). Yield: 1.08 g of 11β-hydroxy-6α-methyl-17,21-dipropionyloxy-4-pregnene-3,20-dione, mp 210° C.

EXAMPLE 10

Analogously to Example 8, 1.0 g of 11β,21-dihydroxy-6α-methyl-17-propionyloxy-4-pregnene-3,20-dione is reacted with 5 ml of butyric anhydride. After precipitation with ice water-sodium chloride, the mixture is extracted with methylene chloride; a steam distillation is conducted, and the mixture is worked up as usual. The crude product is purified by crystallization from acetone-hexane, thus obtaining 912 mg of 21-butyryloxy-11β-hydroxy-6α-methyl-17-propionyloxy-4-pregnene-3,20-dione, mp 211° C.

EXAMPLE 11

(a) A solution of 5.0 g of 21-acetoxy-11β,17-dihydroxy-6α-methyl-4-pregnene-3,20-dione in 25 ml of pyridine is combined at −15° C. dropwise with 3 ml of trifluoroacetic anhydride and stirred for 10 minutes at −10° C. The mixture is poured on an ice water-sodium chloride solution and the precipitate is filtered off. The residue is taken up in methylene chloride, washed neutral, and, after drying over sodium sulfate, concentrated under vacuum. Yield: 5.1 g of 21-acetoxy-17-hydroxy-6α-methyl-11β-trifluoroacetoxy-4-pregnene-3,20-dione.

(b) 3.7 g of the crude product obtained in (a) is stirred in 45 ml of diethylene glycol dimethyl ether and 5.5 ml of propionic anhydride with 5.9 g of 4-dimethylaminopyridine for 18 hours at room temperature. After working up the mixture as usual, 3.9 g of 21-acetoxy-6α-methyl-17-propionyloxy-11β-trifluoroacetoxy-4-pregnene-3,20-dione is isolated.

(c) 2.0 g of 21-acetoxy-6α-methyl-17-propionyloxy-11β-trifluoroacetoxy-4-pregnene-3,20-dione is agitated in 50 ml of methanol and 2.5 ml of triethylamine for 4 hours at room temperature. The crude product is purified on 300 g of silica gel with a methylene chloride-acetone gradient (0–15% acetone), thus isolating 1.2 g of 21-acetoxy-11β- hydroxy-6α-methyl-17-propionyloxy-4-pregnene-3,20-dione.

EXAMPLE 12

Under the conditions of Example 9, 1.0 g of 17-butyryloxy-11β,21-dihydroxy-6α-methyl-4-pregnene-3,20-dione is reacted with acetic anhydride, worked up, and purified. Yield: 1.02 g of 21-acetoxy-17-butyryloxy-11β-hydroxy-6α-methyl-4-pregnene-3,20-dione.

EXAMPLE 13

1.0 g of 17-butyryloxy-11β,21-dihydroxy-6α-methyl-4-pregnene-3,20-dione is reacted analogously to Example 9 with propionic anhydride, worked up, and purified, resulting in 1.1 g of 17-butyryloxy-11β-hydroxy-6α-methyl-21-propionyloxy-4-pregnene-3,20-dione, mp 175° C.

EXAMPLE 14

Under the conditions of Example 10, 1.0 g of 17-butyryloxy-11β,21-dihydroxy-6α-methyl-4-pregenen-3,20-dione is reacted with butyric anhydride and worked up analogously. The crude product is recrystallized from acetone-hexane, thus isolating 860 mg of 17,21-dibutyryloxy-11β-hydroxy-6α-methyl-4-pregnene-3,20-dione, mp 103° C.

EXAMPLE 15

1.0 g of 17-butyryloxy-11β,21-dihydroxy-6α-methyl-4-pregnene-3,20-dione is reacted in pyridine with 5 ml of valeric anhydride as described in Example 10. After performing the usual working-up operation and after purification on 65 g of silica gel with a methylene chloride-acetone gradient (0-15% acetone), 980 mg of 17-butyryloxy-11β-hydroxy-6α-methyl-21-valeryloxy-4-pregnene-3,20-dione is isolated.

EXAMPLE 16

Under the conditions of Example 10, 1.0 g of 11β,21-dihydroxy-17-propionyloxy-6α-methyl-4-pregnene-3,20-dione is reacted with isobutyric anhydride, worked up, and purified. Yield: 870 mg of 11β-hydroxy-21-isobutyryloxy-6α-methyl-17-propionyloxy-4-pregnene-3,20-dione.

EXAMPLE 17

Analogously to Example 9, 1.0 g of 11β,21-dihydroxy-6α-methyl-17-valeryloxy-4-pregnene-3,20-dione is reacted with acetic anhydride, worked up, and purified, thus isolating 980 mg of 21-acetoxy-11β-hydroxy-6α-methyl-17-valeryloxy-4-pregnene-3,20-dione.

EXAMPLE 18

2.9 g of 11β,17-dihydroxy-21-isovaleryloxy-6α-methyl-4-pregnene-3,20-dione is rearranged analogously to Example 4 with lithium dimethyl cuprate, worked up, and purified, thus isolating 1.6 g of 11β,21-dihydroxy-17-isovaleryloxy-6α-methyl-4-pregnene-3,20-dione.

EXAMPLE 19

Under the conditions of Example 9, 1.0 g of 11β,21-dihydroxy-17-isobutyryloxy-6α-methyl-4-pregnene-3,20-dione is reacted with propionic anhydride, worked up, and purified, thus obtaining 985 mg of 11β-hydroxy-17-isobutyryloxy-6α-methyl-21-propionyloxy-4-pregnene-3,20-dione.

EXAMPLE 20

Analogously to Example 9, 2.2 g of 17-benzoyloxy-11β,21-dihydroxy-6α-methyl-4-pregnene-3,20-dione is reacted with acetic anhydride and worked up as usual. The crude product is purified on 350 g of silica gel with a methylene chloride-acetone gradient (0-8% acetone), thus isolating 1.6 g of 21-acetoxy-17-benzoyloxy-11β-hydroxy-6α-methyl-4-pregnene-3,20-dione, mp 210° C.

EXAMPLE 21

1.0 g of 11β,21-dihydroxy-6α-methyl-17-trimethylacetoxy-4-pregnene-3,20-dione is reacted under the conditions of Example 9 with propionic anhydride, worked up, and purified as described above, resulting in 940 mg of 11β-hydroxy-6α-methyl-21-propionyloxy-17-trimethylacetoxy-4-pregnene-3,20-dione.

EXAMPLE 22

Under the conditions of Example 8, 500 mg of 17-acetoxy-11β,21-dihydroxy-6α-methyl-4-pregnene-3,20-dione is reacted with 1.5 ml of acetic anhydride to 480 mg of 17,21-diacetoxy-11β-hydroxy-6α-methyl-4-pregnene-3,20-dione, mp 130°-135° C.

EXAMPLE 23

Under the conditions of Example 8, 500 mg of 17-acetoxy-11β,21-dihydroxy-6α-methyl-4-pregnene-3,20-dione is reacted with 1.5 ml of propionic anhydride in pyridine, thus obtaining 490 mg of 17-acetoxy-11β-hydroxy-6α-methyl-21-propionyloxy-4-pregnene-3,20-dione, mp. 99°-103° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. 21-Acetoxy-17α-butyryloxy-11β-hydroxy-6α-methyl-4-pregnene-3,20-dione.

2. A pharmaceutical composition comprising an antiinflammatorily effective amount of the compound of claim 1 and at least one pharmaceutically acceptable carrier.

3. A composition of claim 2 which is topically administerable.

4. A method of treating inflammation in a patient in need of such treatment comprising administering to the patient an antiinflammatory effective amount of the compound of claim 1.

5. A method of claim 4, wherein the administration is topical.

* * * * *